United States Patent [19]
Allen et al.

[11] Patent Number: 5,235,067
[45] Date of Patent: Aug. 10, 1993

[54] CONTINUOUS PROCESS FOR ALKENYL SUCCINIMIDES

[75] Inventors: Billy R. Allen, Bridge City; Bobby R. Martin, Beaumont; John A. Lemen; Leonard A. Matthews, both of Port Arthur, all of Tex.

[73] Assignee: Texaco Inc., White Plains, N.Y.

[21] Appl. No.: 431,053

[22] Filed: Nov. 3, 1989

[51] Int. Cl.$^5$ .............................................. C07D 207/40
[52] U.S. Cl. .................................... 548/520; 548/545; 252/51.5 A
[58] Field of Search .............................. 548/520, 545; 252/51.5 A

[56] References Cited

U.S. PATENT DOCUMENTS

| | | | |
|---|---|---|---|
| 4,364,846 | 12/1982 | Kaufman | 562/561 |
| 4,636,322 | 1/1987 | Nalesnik et al. | 252/51.5 A |
| 4,699,724 | 10/1987 | Nalesnik et al. | 252/51.5 A |
| 4,713,189 | 12/1987 | Nalesnik et al. | 252/51.5 A |

*Primary Examiner*—C. Warren Ivy
*Assistant Examiner*—Celia Chang
*Attorney, Agent, or Firm*—Jack H. Park; Kenneth R. Priem; Richard A. Morgan

[57] ABSTRACT

A continuous process has been found for producing hydroxyacylated alkenyl-substituted mono- and bis-succinimides. The Mannich phenol coupled compositions are produced continuously as well. In the imidization reaction, an alkenyl succinic anhydride is contacted with a polyamine to form mono- and bis- polyamino alkenyl succinimides in continuous stirred tank reactor for a residence time of 1 to 3 hours. The reaction product is then, optionally Mannich base coupled. Finally, in the amidization, the mono- and bis- polyamino alkenyl succinimide is contacted with an acylating agent such as hydroxyacetic acid. Contacting is carried out in a continuous stirred tank reactor for a residence time of 3 to 6 hours. A hydroxyacylated alkenyl-substituted mono- and bis- succinimide product free of haze is produced in the absence of filtering, by reducing water continuously in all three reactors to a concentration of 0.4 wt %.

2 Claims, No Drawings

CONTINUOUS PROCESS FOR ALKENYL SUCCINIMIDES

BACKGROUND OF THE INVENTION

1. Field of the Invention

The invention is a continuous process for preparing modified succinimides. These modified succinimides are used as dispersants in lubricating oils for internal combustion engines.

2. Description of Methods in the Field of the Invention

Internal combustion engines operate under a wide range of temperatures including low temperature stop-and-go service as well as high temperature conditions produced by continuous high speed driving. Stop-and-go driving, particularly during cold, damp weather conditions, leads to the formation of a sludge in the crankcase and in the oil passages of a gasoline or a diesel engine. This sludge seriously limits the ability of the crankcase oil to effectively lubricate the engine. In addition, the sludge with its entrapped water tends to contribute to rust formation in the engine. These problems tend to be aggravated by the manufacturer's lubrication service recommendations which specify extended oil drain intervals.

It is known to employ nitrogen containing dispersants and/or detergents in the formulation of crankcase lubricating oil compositions. Many of the known dispersant/detergent compounds are based on the reaction of an alkenylsuccinic acid or anhydride with an amine or polyamine to produce an alkylsuccinimide or an alkenylsuccinamic acid a determined by selected conditions of reaction.

T. J. Karol et al. U.S. Pat. No. 4,482,464 teaches hydrocarbyl-substituted mono- and bis- succinimides comprising a polyamine chain linking hydroxyacyl radicals. These compositions are compounded with a mineral oil to produce a lubricant composition.

T. E. Nalesnik U.S. Pat. No. 4,636,322 teaches Mannich phenol coupled glycamide bis-alkenyl succinimides. These compounds are synthesized step wise in a batch process. The compounds are effective as dispersants when incorporated in a minor proportion in lubricating oil.

T. E. Nalesnik et al U.S. Pat. No. 4,713,189 teaches a lubricating oil dispersant prepared by coupling two polyethyleneamine moieties with an aldehyde and a phenol, followed by conversion to a succinimide. The resulting coupled succinimide is then acylated with glycolic acid to form a glycolated Mannich phenol coupled mono-alkenyl succinimide. These dispersants are synthesized stepwise in a batch process.

R. H. Wollenberg et al U.S. Pat. Nos. 4,612,132 and 4,747,965 teach modified polyamino alkenyl and alkyl succinimides. These compounds are prepared by a continuous process. According to the continuous process, an alkenyl or alkyl succinic anhydride is contacted with a polyamine to form a polyamino alkenyl or alky succinimide. This composition is contacted with a cyclic carbonate to form the modified polyamino alkenyl or alkyl succinimide. Water is removed from the reaction system either before or during the course of the reaction via azeotroping or distillation.

SUMMARY OF THE INVENTION

The invention is a continuous process for preparing hydroxyacylated alkenyl-substituted mono- and bis- succinimides in the absence of filtering. In the process an alkenyl succinic anhydride is contacted with a polyamine to form of mono- and bis- polyamino alkenyl succinimides reaction intermediate. The reaction is carried out in a first continuous stirred tank reactor for a residence time of about 1 to 3 hours at a temperature sufficient to cause reaction. The molar ratio of alkenyl succinic anhydride to polyamine is about 1:1 to 2:1. The mono-and bis- polyamino alkenyl succinimides may optionally be Mannich phenol coupled. Mannich phenol coupling is carried out by reaction with equimolar quantities of aldehyde and hal quantities of phenol to form a reaction intermediate.

Either reaction intermediate is passed to a final continuous stirred tank reactor wherein it is acylated with an acylating agent for a residence time of 3 to 6 hours at a temperature sufficient to cause reaction. The molar ratio of mono- and bis- polyamino alkenyl succinimide to acylating agent is 0.1:1 to 10:1.

Water is removed continuously in all three reactions to maintain a water concentration of 0.4 wt % or less in the acylation reaction, thereby producing a haze free product in the absence of filtering.

DESCRIPTION OF THE PREFERRED EMBODIMENTS

Imidization Reaction

The alkenyl-substituted mono- and bis- polyamino succinimide synthesized according to the inventive process is represented by the formula:

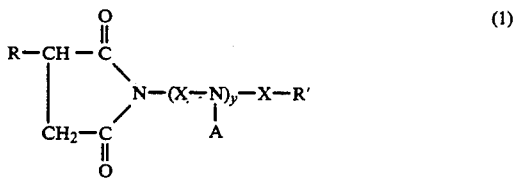

(1)

In this formula R is an alkenyl radical having from about 8 to 400 carbon atoms and preferably having from 50 to 200 carbon atoms. X is a divalent alkylene or secondary hydroxy-substituted alkylene radical having from 2 to 3 carbon atoms. A is hydrogen or a hydroxyacyl radical preferably selected from the group consisting of glycolyl, lactyl, 2-hydroxymethyl propionyl and 2, 2' bis - hydroxymethyl propionyl radicals. It is preferred that at least about 30% of the A radicals are the hydroxyacyl radicals. The integer y ranges from 1 to 6 and preferably ranges from 2 to 4. R' is a radical selected from the group consisting of—$NH_2$—NHA or the alkenyl substituted succinyl radical having the formula:

(2)

It is apparent that when R' is the alkenyl substituted succinyl radical, that the bis-polyamino alkenyl succinimide compounds are represented.

These mono- and bis- polyamino alkenyl succinimides are prepared by reacting an alkenyl succinic anhydride with a polyamine. The alkenyl succinic anhydride may be characterized by the formula:

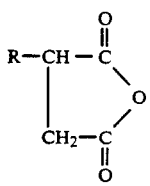 (3)

Wherein R is an alkenyl radical ranging in molecular weight from about 500 to about 4000, preferably about 1000 to about 2100. These succinic acid anhydrides are synthesized by reacting a polyolefin from which the alkenyl radical R is derived with maleic acid anhydride to form the alkenyl succinic acid anhydride.

The polyamines may be characterized by the formula:

 (4)

In this formula, a is an integer of about 1 to 6, and n is the integer 0 or 1.

In the polyamine, R' may be hydrogen or a hydrocarbon radical selected from the group consisting of alkyl, aralkyl, cycloalkyl, aryl, alkaryl, alkenyl, and alkynyl including such radicals when inertly substituted. When R' is alkyl, it may typically be methyl, ethyl, n-propyl, iso-propyl, n-butyl, i-butyl, sec-butyl, amyl, octyl, decyl, octadecyl, etc. When R' is aralkyl, it may typically be benzyl, beta-phenylethyl, etc. When R' is cycloalkyl, it may typically be cyclohexyl, cycloheptyl, cyclooctyl, 2-methylcyclo-heptyl, 3-butylcyclohexyl, 3-methylcyclohexyl, etc. When R' is aryl, it may typically be phenyl, naphthyl, etc. When R' is alkaryl, it may typically be tolyl, xylyl, etc. When R' is alkenyl, it may typically be allyl, 1-butenyl, etc. When R' is alkynyl, it may typically be ethynyl, propynyl, butynyl, etc. R' may be inertly substituted i.e. it may bear a non-reactive substituent such as alkyl, aryl, cycloalkyl, ether, halogen, nitro, etc. Typically inertly substituted R' groups may include 3-chloropropyl, 2-ethoxyethyl, carboethoxymethyl, 4-methyl, cyclohexyl, p-chlorophenyl, 2-chlorobenzyl, 3-chloro-5-methylphenyl, etc. The preferred R' groups may be hydrogen or lower alkyl, i.e. $C_1$-$C_{10}$ alkyl, groups including e.g. methyl, ethyl, n-propyl, i-propyl, butyls, amyls, hexyls, octyls, decyls, etc. R' may preferably be hydrogen.

R" may be a hydrocarbon selected from the same group as R' subject to the fact that R" is divalent and contains one less hydrogen. Preferably R' is hydrogen and R" is —$CH_2CH_2$—.

Typical polyamines which may be employed may include ethylene diamine, propylene diamine, diethylenetriamine, triethylenetetramine, and tetraethylenepentamine. The most preferred amine is pentaethylenehexamine.

The reaction of the alkenyl succinic anhydride with polyamine is carried out in a continuous stirred tank reactor (CSTR). Alkenyl succinic anhydride and polyamine are fed continuously to the reactor in a molar ratio of 1:1 to 2:1. The flow rates of reactants should be in proportion to the size of the reactor to give a residence time of about 1 to 3 hours.

The reaction is carried out at a temperature sufficient to cause reaction which is generally in the range of 0° C. to 250° C.; preferably 125° C. to 200° C.; most preferably 150° C. to 180° C.

The imidization reaction yields water. It is essential to remove water during the course of the reaction to drive the reaction to completion, using all available polyamine. Residual polyamine carried over to the amidization reaction reacts with the carboxylic acid moiety of the acylating agent to produce haze forming amine salts. Water is removed continuously preferably to a concentration of 0.4 wt % or less. Water removal is achieved by means of azeotroping, distillation or azeotropic distillation. Additional interstage water removal such as by distillation between two reaction stages is feasible.

Mannich Coupling Reaction

If a Mannich coupled final product is required, the mono- and bis- polyamino alkenyl-substituted succinimide of the imidization reaction is passed directly to a continuous stirred tank reactor (CSTR) for the Mannich base reaction.

Typical aldehydes which are employed include formaldehyde, ethanal, propanal and butanal. The preferred aldehyde is formaldehyde in the polymer paraformaldehyde form.

The charge phenols which are employed may be characterized by the formula $HR_3OH$. These phenols must contain an active hydrogen to provide an active site for substitution. Poly-phenols, such as those containing more than one hydroxy group in the molecule may be used as well. The rings on which the hydroxy groups are positioned may bear inert subsituents. However, at lease two positions, such as ortho and para, to a phenol hydroxy group, must be occupied by an active hydrogen as this is the point of reaction with the reaction product of the imidization reaction.

$R_3$ may be an arylene group such as—$C_6H_4$—,—$C_6H_3(CH_3)$— and—$C_6H_3(C_2H_5)$—.

Typical phenols which are employed according to the invention include, phenol, bisphenol A, resorcinol, mono-nonyl phenol and beta-naphthol. The preferred phenols are phenol and mono-nonyl phenol.

The Mannich coupling reaction is carried out continuously in a continuous stirred tank reactor (CSTR). The imide reaction product, aldehyde and phenol are fed continuously to the reactor. The aldehyde is added in molar excess of the number of moles of polyamine from the imide reaction. The phenol is added in half molar quantities relative to the polyamine from the imide reaction. The continuous stirred tank reactor (CSTR) is of a size to give a residence time of 1 to 3 hours.

The reaction is carried out at temperature sufficient to cause reaction which is generally in the range of 0° C. to 250° C.; preferably 125° C. to 200° C.; most preferably 150° C. to 180° C.

It is essential to remove water continuously during the course of the reaction. This facilitates the reduction of water to the required concentration in the amidization reaction where it is absolutely critical to produce a haze free product. Water is preferably removed continuously to a concentration of 0.4 wt % or less. Water removal is achieved by means of distillation or azeotropic distillation. In addition, interstage water removal such as by continuous distillation between continuous stirred tank reactors may be used.

Amidization Reaction

Finally, the reaction product of the imidization reaction which is optionally Mannich coupled is fed continuously to a continuous stirred tank reactor (CSTR).

The preferred acylating agents which are carboxylic acids are glycolic acid, oxalic acid, lactic acid, 2-hydroxymethyl propionic acid and 2,2-bis(hydroxymethyl) propionic acid. The most preferred acylating agents are glycolic acid and oxalic acid.

The reaction is carried out by feeding the reactants continuously to the continuous stirred tank reactor in a molar ratio of 0.1:1 to 10:1 acylating agent: active amine. For example, when tetraethylenepentamine is employed as the polyamine in the imidization reaction, 1.7 moles of glycolic acid are added per mole of tetraethylenepentamine. Similarly, when triethylenetetramine is used, about 0.7 moles of glycolic acid is added. When pentaethylenehexamine is employed, about 2 to 7 moles of glycolic acid are added per mole of polyamine.

Acylation is carried out at about 100° C. to 180° C., preferably about 160° C. in the presence of an excess of inert, diluent solvent. The rates are adjusted to give a residence time in the range of 3 to 6 hours.

In the acylation reaction, the carboxyl group of the acylating agent bonds to nitrogen atom from the polyamine residing in the imidization reaction product. Molar quantities of water are a by-product of the reaction. When water is not removed from the reaction mixture during reaction, coreactions are enhanced. Specifically, the imide reaction product combines with water to yield the original polyamine. This polyamine reacts with the carboxylic acid from the acylating agent to yield insoluble amine salts. These insoluble amine salts are detected as haze in the amidization reaction product. Haze is removed by filtering. Applicants have found that when the concentration of water is maintained below 0.4 wt %, typically 0.1 wt % to 0.4 wt %, that a product, reduced in haze is produced. The reduction is so reproducible that a commercially acceptable product is yielded in the absence of a filtering stage.

In order to produce this haze free product, it is essential to remove water to a low concentration during the amidization reaction. This is achieved by flash distillation. In flash distillation, reaction temperature is adjusted, at atmospheric pressure, to vaporize the water which is continuously removed as a vapor by-product. Flash distillation is facilitated by limiting the amount of water in the amidization reaction mixture. This is achieved as described by removing water during upstream processing.

The invention is shown by way of example.

Glycolated Succinimide

EXAMPLE 1A (COMPARATIVE)

Batch Process

Hydroxyacylated alkenyl-substituted mono- and bis-succinimides were prepared according to T. J. Karol et al. U.S. Pat. No. 4,482,464.

A 174 lb. (0.0884 mole) quantity of 1968.4 molecular weight alkenyl succinic acid anhydride was reacted in a stirred batch reactor with 15.0 lb. (0.0577 mole) pentaethylenehexamine in oil. The mixture was heated to about 230° F. and held for 1.58 hr. with nitrogen blowing to remove water.

Then 20.8 lb. (0.2010 mole) of 73% glycolic acid in water was added. The admixture had a water concentration of about 1.6 wt %. The admixture was heated to about 320° F. and held with nitrogen blowing until the concentration of water dropped to the 0.1 wt % to 0.4 wt % range, which took 6.75 hr.

A sample of the crude product was prepared with SNO-7 oil. The prepared sample had a Lumetron Turbidity (haze) of 23.5. The crude product was polish filtered with 3.8 lb. of filter aid. A sample of the filtered product was prepared and had a lumetron Turbidity (haze) of 2.0.

The results of the batch process were as follows:

1. Charge Quantities

|  | Weight Lbs | Molecular Weight | Lb Moles |
|---|---|---|---|
| ASAA (57 SAP) | 174.0 | 1968.4 | 0.0884 |
| PEHA | 15.0 | 260.0 | 0.0577 |
| 100 P PALE OIL | 160.2 | — | — |
| Glycolic Acid (73% in water) | 20.8 | 76.0 | 0.2010 |
| Filter Aid | 3.8 | — | — |
| TOTAL | 373.8 |  |  |

2. Recovery

|  | Weight Lbs |
|---|---|
| Overheads | 9.7 |
| Filtered Product | 338.2 |
| Samples | 14.9 |
| Filter Cake | 11.0 |
| Slop | 0.0 |
| Loss | 0.0 |
| TOTAL | 373.8 |

3. Time-Temperature Cycle

| STEP | Time, Hrs | Temp., °F. |
|---|---|---|
| 1. Charge Pale Oil + PEHA | 0.58 | ambient |
| 2. Charge ASAA | 0.34 | ambient–200 |
| 3. Heating | 0.58 | 200–230 |
| 4. Imidization Reaction | 1.00 | 229–231 |
| 5. Charge Glycolic Acid | 0.25 | 231 |
| 6. Heating | 2.75 | 231–320 |
| 7. Glycolation Reaction | 4.00 | 317–321 |
| TOTAL | 9.50 |  |

4. Test Results

| Test | Method ASTM | Crude Products | Filtered Product |
|---|---|---|---|
| Saponification No. (SAP) Modified | D-94 |  |  |
| Specific Gravity @ 60/60° F. | D-1298 | 0.923 | 0.923 |
| Color, ASTM Dilute | D-1500 | 5.5 | 5.5 |
| Nitrogen | Kjeldahl | 1.45 wt % | 1.39 wt % |
| Total Base Number | D-2896 | 18.2 | 17.4 |
| Total Acid Number | D-974 | 4.9 | 3.88 |
| Kinematic Viscosity, | D-445 | 123 cSt | 110 cSt |
| Lumetron Turbidity (Clarity) (10 Vol % in SNO-7 Oil) |  | 23.5 | 2.0 |
| Water | D-95 | — | <0.1 wt % |

ASAA - alkenyl succinic acid anhydride
PEHA - pentaethylenehexamine

EXAMPLE 1B

Continuous Stirred Tank Reactor Synthesis

Hydroxyacylated alkenyl-substituted mono- and bis-succinimides were prepared in two continuous stirred tank reactors.

Imidization

Alkenyl succinic acid anhydride (2431.35 gram molecular weight) was added continuously to a 60 gallon continuous stirred tank reactor at a rate of 1048.00 ml/min. (0.40 mole/min.) along with 70.10 ml/min. (0.27 mole/min.) of pentaethylenehexamine and oil. The reactor temperature was maintained with heating at a temperature of about 275° F. for a residence time of about 2 hours. The reactor was continuously blown with nitrogen to remove water.

Amidization

The reaction product was recovered and passed to a 60 gallon continuous stirred tank reactor at a rate of 787.00 ml/min. along with 35.77 ml/min. (0.42 moles/min.) of glycolic acid in water. Reactor temperature was maintained with heating at a temperature of about 377° F. for a residence time of about 4.72 hours. The reactor was continuously blown with nitrogen to give a water concentration of 0.4 wt %. A prepared sample of the recovered product demonstrated a Lumetron Turbidity (haze) of 9.5 in the absence of filtering.

Results of the process were as follows:

1. Imidization Reaction

| a. Charge | ml/min @ 60° F. | Grams/min | moles/min |
|---|---|---|---|
| ASAA (46.5 SAP) | 1048.00 | 972.54 | 0.40 |
| PEHA | 70.10 | 70.80 | 0.27 |
| 100 P Pale Oil | 776.24 | 685.81 | — |
| b. Conditions | | | |
| Test Period Time | 240 min | | |
| Retention Volume | 60 gal. | | |
| Retention Time | 2 hrs. | | |
| Reactor Temperature | 275° F. | | |

2. Glycolation Reaction

| a. Charge | ml/min @ 60° F. | Grams/min | moles/min |
|---|---|---|---|
| Imide | 787.00 | 710.03 | — |
| Glycolic Acid (70.4% in water) | 35.77 | 45.43 | 0.42 |
| b. Conditions | | | |
| Test Period Time | 540 min. | | |
| Retention Volume | 60 gal. | | |
| Retention Time | 4.72 hrs | | |
| Reactor Temperature | 377° F. | | |

3. Test Results

| Test | ASTM Method | Crude Product |
|---|---|---|
| Specific Gravity, @ 60/60° F. | D-1298 | 0.915 |
| Color, ASTM Dilute | D-1500 | 5.5 |
| Nitrogen | Kjeldahl | 1.36 wt % |
| Total Base Number | D-2896 | 15.6 |
| Total Acid Number | D-974 | 5.1 |
| Kinematic Viscosity | D-445 | 179 cSt |
| Lumetron Turbidity (Clarity) (10 Vol % in SNO-7 Oil) | | 9.5 |
| Water | D-95 | 0.4 wt % |

EXAMPLE 2A (COMPARATIVE)

Batch Process

Mannich Base Coupled Glycolated Succinamide

Mannich phenol coupled hydroxyacylated alkenyl-substituted mono- and bis- succinimides were prepared according to T. E. Nalesnik U.S. Pat. No. 4,636,322.

A 421.0 lb. (0.1201 mole) quantity of 3506 molecular weight alkenyl succinic acid anhydride was reacted in a stirred batch reactor with 16.2 lb. (0.0611 mole) pentaethylenehexamine in oil. The mixture was heated to about 248° F. and held for 9.00 hours with nitrogen blowing to remove water.

First 6.9 lb. (0.0314 mole) nonylphenol was added at the reactor temperature of 254° F. Then 10 lb. (0.1233 mole) of 37% formaldehyde in water was added and the reaction mixture held without heating for a total of 1.75 hours with nitrogen blowing to remove water.

Then 18.0 lb. (0.1667) of 70.4% glycolic acid in water was added. The admixture had a water concentration in the range of about 0.6 wt % to 0.8 wt %. The admixture was heated to about 20° F. and held with nitrogen blowing until the concentration of water dropped to the range of 0.1 wt % to 0.4 wt %, which took about 8 hours.

A prepared sample of the crude product had a Lumetron Turbidity (haze) of 13.0. The crude product was polish filtered with 12.0 lb. of filter aid. A prepared sample of the filtered product was prepared and had a Lumetron Turbidity (haze) of 4.0.

The results of the batch process are as follows:

1. Charge Quantities

| | Weight, Lbs | Molecular Weight | Lb Moles |
|---|---|---|---|
| ASAA (32 SAP) | 421.0 | 3506 | 0.1201 |
| PEHA | 16.2 | 265 | 0.0611 |
| 100 P PALE OIL | 358.0 | — | — |
| Nonylphenol | 6.9 | 220 | 0.0314 |
| Formaldehyde (37% in water) | 10.0 | 30 | 0.1233 |
| Glycolic Acid (70.4% in water) | 18.0 | 76 | 0.1667 |
| Filter Aid | 12.0 | — | — |
| TOTAL | 842.1 | | |

2. Recovery

| | Weight, Lbs |
|---|---|
| Overheads | 15.3 |
| Filtered Product | 741.0 |
| Samples | 6.5 |
| Filter Cake | 30.1 |
| Slop | 39.7 |
| Loss | 9.3 |
| TOTAL | 842.1 |

3. Time-Temperature Cycle

| STEP | Time, Hrs | Temp., °F. |
|---|---|---|
| 1. Charge ASAA | 1.00 | 110–160 |
| 2. Charge PEHA | 0.25 | 160 |
| 3. Heating | 7.00 | 160–248 |
| 4. Imidization Reaction | 2.00 | 248–254 |
| 5. Charge Nonylphenol | 0.25 | 254 |
| 6. Charge Formaldehyde | 1.00 | 250–235 |
| 7. Mannich Base Reaction | 0.50 | 235 |
| 8. Charge Glycolic Acid | 0.80 | 235–250 |
| 9. Heating | 2.00 | 250–320 |
| 10. Glycolation Reaction | 4.00 | 320–321 |
| 11. Cool and Add Pale Oil | 4.00 | 320–250 |
| TOTAL | 22.80 | |

4. Test Results

| Test | ASTM Method | Crude Product | Filtered Product |
|---|---|---|---|
| Saponification No. (SAP) Modified | D-94 | | |
| Specific Gravity, @ 60/60° F. | D-1298 | — | 0.9003 |
| Color, ASTM Dilute | D-1500 | — | <3.0 |
| Nitrogen | Kjeldahl | — | 0.70 wt % |
| Total Base Number | D-2896 | — | 8.80 |
| Total Acid Number | D-974 | — | 2.80 |
| Kinematic Viscosity | D-445 | — | 175 cSt |
| Lumetron Turbidity, (Clarity)(10 Vol % in SNO-7 Oil) | | 13.0 | 4.0 |
| Water | D-95 | — | 0.2 wt % |

EXAMPLE 2B

Continuous Stirred Tank Reactor Synthesis

Mannich phenol coupled hydroxyacylated alkenyl-substituted mono- and bis- succinimides were prepared in three continuous stirred tank reactors.

Imidization

Alkenyl succinic acid anhydride (3789.9 gram molecular weight) was added continuously to a 60 gallon continuous stirred tank reactor at a rate of 1266.0 ml/min. (0.31 moles/min.) along with 45.54 ml/min. (0.17 mole/min.) of pentaethylenehexamine and oil. The reactor was maintained with heating at a temperature of about 246° F. for a residence time of about 1.74 hours. The reactor was continuously blown with nitrogen to remove water.

Mannich Coupling

The reaction product was recovered and passed to a 60 gallon continuous stirred tank reactor at a rate of 1856.0 ml/min. along with 17.55 ml/min. (0.08 mole/min.) of nonylphenol and 20.61 ml/min. (0.28 mole/min.) formaldehyde in water. Reactor temperature was maintained with heating at a temperature of about 255° F. for a residence time of about 2.02 hours. The reactor was continuously blown with nitrogen to remove water.

Amidization

The reaction product was recovered and passed to two 60 gallon continuous stirred tank reactors in series at a rate of 1855.0 ml/min. Glycolic acid in water was passed to the first reactor at 32.25 ml/min. (0.38 mole/min.). Both reactor temperatures were maintained with heating at about 355° F. and the residence time of each reactor was about 2.02 hours. Both reactors were blown continuously with nitrogen to maintain water concentration in the range of 0.1 wt % to 0.4 wt %.

A prepared sample of the second reactor effluent demonstrated a Lumetron Turbidity (haze) of 3.0 in the absence of filtering.

Results of the process were as follows:

1. Imidization Reaction

| a. Charge | ml/min @ 60° F. | Grams/min | moles/min |
|---|---|---|---|
| ASAA (30 SAP) | 1266.00 | 1174.85 | 0.31 |
| PEHA | 45.54 | 46.00 | 0.17 |
| 100 P Pale Oil | 860.00 | 759.81 | — |
| b. Conditions | | | |
| Test Period Time | 2460 min | | |
| Retention Volume | 60 gal. | | |
| Retention Time | 1.74 hrs | | |
| Reactor Temperature | 246° F. | | |

2. Mannich Base Reaction

| a. Charge | ml/min @ 60° F. | Grams/min | moles/min |
|---|---|---|---|
| Imide | 1856.00 | 1670.40 | — |
| Nonylphenol | 17.55 | 16.73 | 0.08 |
| Formaldehyde (32% in water) | 20.61 | 22.98 | 0.28 |
| b. Conditions | | | |
| Test Period Time | 2520 min. | | |
| Retention Volume | 60 gal. | | |
| Retention Time | 2.02 hrs. | | |
| Reactor Temperature | 255° F. | | |

3. Glycolation Reaction

| a. Charge | ml/min @ 60° F. | Grams/min | moles/min |
|---|---|---|---|
| Mannich Base | 1855.00 | 1676.92 | — |
| Glycolic Acid (70.4% in water) | 32.25 | 40.96 | 0.38 |
| b. Conditions | | | |
| Test Period Time | 360 min. | | |
| FIRST REACTOR | | | |
| Retention Volume | 60 gal. | | |
| Retention Time | 2.02 hrs | | |
| Reactor Temperature | 255° F. | | |
| SECOND REACTOR | | | |
| Retention Volume | 60 gal. | | |
| Retention Time | 2.02 hrs | | |
| Reactor Temperature | 255° F. | | |

4. Test Results

| Test | ASTM Method | Crude Product |
|---|---|---|
| Saponification No. (SAP) Modified | D-94 | |
| Specific Gravity, @ 60/60° F. | D-1298 | 0.9081 |
| Color, ASTM Dilute | D-1500 | <4.5 |
| Nitorgen | Kjeldahl | 0.72 wt % |
| Total Base Number | D-2896 | 10.00 |
| Total Acid Number | D-974 | 2.7 |
| Kinematic Viscosity | D-445 | 304 cSt |
| Lumetorn Turbidity (Clarity) (10 Vol % in SNO-7 Oil) | | 3.0 |
| Water | D-95 | 0.4 wt % |

While particular embodiments of the invention have been described, it will be understood, of course, that the invention is not limited thereto since many modifications may be made, and it is, therefore, contemplated to cover by the appended claims any such modification as fall within the true spirit and scope of the invention.

What is claimed is:

1. A continuous process for preparing hydroxyacylated alkenyl-substituted mono- and bis- succinimides which comprises:
   (a) continuously contacting an alkenyl succinic anhydride with a polyamine to form mono- and bis- polyamino alkenyl succinimides, while removing water in a first continuous stirred tank reactor for a residence time of about 1 to 3 hours at a temperature sufficient to cause reaction wherein the molar ratio of the alkenyl succinic anhydride to polyamine is from 1:1 to 2:1, and
   (b) continuously acylating the mono- and bis- polyamino alkenyl succinimide with an acylating agent to form hydroxyacylated hydrocarbyl-substituted mono- and bis- succinimides, while removing water to maintain a water concentration of 0.4 wt % or less in a second continuous stirred tank reactor for a residence time of about 3 to 6 hours at a temperature sufficient to cause reaction, wherein the molar ratio of mono- and bis- polyamino alkenyl succinimide to acylating agent is from 0.1:1 to 10:1,
   (c) thereby yielding haze free hydroxyacetylated alkenyl-substituted mono- and bis- succinimides in the absence of filtering.

2. The process of claim 1 wherein step(a) water is removed to a concentration of 0.4 wt % or less.

* * * * *